(12) United States Patent
Kim et al.

(10) Patent No.: US 11,753,489 B2
(45) Date of Patent: Sep. 12, 2023

(54) NANOPARTICLES USING ANIONIC POLYMER, PREPARATION METHOD AND COMPOSITION THEREOF

(71) Applicant: IMGT CO, LTD., Gyeonggi-do (KR)

(72) Inventors: Seung Ki Kim, Gyeonggi-do (KR); Hyun Ryoung Kim, Gyeonggi-do (KR); Eun Ah Jung, Seoul (KR); Woo Ram Cho, Gyeonggi-do (KR)

(73) Assignee: IMGT CO, LTD., Gyeonggi-do (KR)

( * ) Notice: Subject to any disclaimer, the term of this patent is extended or adjusted under 35 U.S.C. 154(b) by 181 days.

(21) Appl. No.: 17/171,060

(22) Filed: Feb. 9, 2021

(65) Prior Publication Data

US 2022/0089795 A1 Mar. 24, 2022

(30) Foreign Application Priority Data

Sep. 22, 2020 (KR) .................. 10-2020-0122036

(51) Int. Cl.
| | |
|---|---|
| *C08F 116/06* | (2006.01) |
| *A61K 31/704* | (2006.01) |
| *C08F 2/22* | (2006.01) |
| *C08K 5/1545* | (2006.01) |
| *A61P 35/00* | (2006.01) |
| *B82Y 5/00* | (2011.01) |
| *B82Y 40/00* | (2011.01) |

(52) U.S. Cl.
CPC .......... *C08F 116/06* (2013.01); *A61K 31/704* (2013.01); *A61P 35/00* (2018.01); *C08F 2/22* (2013.01); *C08K 5/1545* (2013.01); *B82Y 5/00* (2013.01); *B82Y 40/00* (2013.01)

(58) Field of Classification Search
CPC ............ A61P 35/00; B82Y 5/00; A61K 45/00
See application file for complete search history.

(56) References Cited

U.S. PATENT DOCUMENTS

| | | | |
|---|---|---|---|
| 2008/0206150 A1* | 8/2008 | Louie ................ | B82Y 5/00 977/773 |
| 2008/0254078 A1 | 10/2008 | Kauper | |
| 2011/0082427 A1 | 4/2011 | Golzarian | |
| 2011/0229580 A1 | 9/2011 | Srivastava | |
| 2015/0231269 A1* | 8/2015 | Kaittanis ............ | A61K 49/1854 514/263.24 |
| 2016/0166716 A1 | 6/2016 | Irudayaraj | |
| 2022/0324988 A1* | 10/2022 | Zhang ................ | A61K 39/3955 |
| 2022/0330396 A1* | 10/2022 | Kühn .................. | A61M 11/042 |

FOREIGN PATENT DOCUMENTS

| | | |
|---|---|---|
| CN | 1917859 A | 2/2007 |
| CN | 104780912 | 7/2015 |
| EP | 1698329 A1 | 9/2006 |
| EP | 2921166 A1 | 9/2015 |
| EP | 3970703 | 3/2022 |
| KR | 1020040020679 | 3/2004 |
| KR | 1020140107179 | 9/2014 |
| KR | 20200087722 | 7/2020 |

OTHER PUBLICATIONS

Kwon, Jung Hyun, "Topics related to clinical hepatocellular carcinoma", The Korean Journal of Hepatology, 2010, 16:242-246.
Huei et al., 2016, "Iron Cross-Linked Carboxymethyl Cellulose-Gelatin Complex Coacervate Beads for Sustained Drug Delivery", 70:243-252.
Bowen P: "Particle Size Distribution Measurement from Millimeters to Nanometers and from Rods to Platelets", Journal of Dispersion Science and Technology, Taylor and Francis Group, New York, NY, US, vol. 23, No. 5, Jan. 1, 2002 (Jan. 1, 2002), pp. 631-662, XP009102859, ISSN: 0193-2691, DOI: 10.1081/DIS-120015368.
Extended European Search Report for App. No. EP21189428.2, dated Feb. 7, 2022, 8 pages.
Japanese Office Action (including English translation) issued in App. No. JP2021-015076, dated Mar. 11, 2022, 8 pages.
Benhalima et al., "Eco-friendly porous carboxymethyl cellulose/dextran sulfate composite beads as reusable and efficient adsorbents of cationic dye methylene blue", International Journal of Biological Macromolecules, No. 132, pp. 126-141, 2019.
English translation of Chinese Office Action issued in App. No. CN202110252978, dated Dec. 23, 2022, 9 pages.

\* cited by examiner

*Primary Examiner* — Andrew S Rosenthal
(74) *Attorney, Agent, or Firm* — Riverside Law LLP

(57) ABSTRACT

The present invention relates to novel nanoparticles using an anionic polymer, a preparation method thereof, a composition, and the like, and the present invention is used for a method of necrosing cancer cells by blocking major blood vessels that supply nutrients to cancer cells to induce an embolic effect, and thus may be used for the treatment of patients with cancer.

15 Claims, 9 Drawing Sheets

Composition 1

Composition 2

Composition 3

NANOPARTICLES USING ANIONIC POLYMER, PREPARATION METHOD AND COMPOSITION THEREOF

CROSS-REFERENCE TO RELATED APPLICATION

This application claims priority to and the benefit of Korean Patent Application No. 10-2020-0122036, filed on Sep. 22, 2020, the disclosure of which is incorporated herein by reference in its entirety.

BACKGROUND

1. Field of the Invention

The present invention relates to novel nanoparticles using an anionic polymer, a preparation method thereof, and the like, and the present invention is used for a method of necrosing cancer cells by blocking major blood vessels that supply nutrients to cancer cells to induce an embolic effect, and thus may be used for the treatment of patients with cancer.

2. Discussion of Related Art

Liver cancer is a malignant tumor with a poor prognosis, ranking second in Korea and third highest in the world among causes of death from carcinoma. Radical surgery is not possible in 70% or more of patients with liver cancer, and even when radical resection is performed, there is a 50% or higher chance of recurrence in other parts of the body within 5 years. The possibility of responding to systemic anticancer therapy in advanced liver cancer is lower than 10% which is extremely low, and as an alternative to this, various image-guided therapies have been developed as non-surgical treatment methods. There are two representative image-guided therapies applied to liver cancer, one is transarterial chemoembolization (TACE) which is a therapeutic method in which an anticancer drug is locally injected into liver cancer through the hepatic artery and embolization is performed on the hepatic artery in parallel, and the other is radiofrequency ablation (RFA).

95% or more of the blood flow supplied to liver cancer tissues is delivered by the hepatic artery, but 75% or more of the blood flow supplied to the surrounding healthy tissues is delivered by the hepatic portal vein, and only 25% of the blood flow is delivered by the hepatic artery, so that the TACE is a safe and effective treatment therapeutic method that does not damage normal tissues.

Since the TACE is typically performed repeatedly 3 and 4 times a year, the substance to be administered is required to be safe. Drugs typically used for existing arterial embolization are doxorubicin, cisplatin, epirubicin, mitoxantron, mitomycin C, and the like, and since these anticancer agents cannot be directly dissolved in a water-insoluble contrast medium, they are dissolved in a water-soluble contrast medium such as Pamiray, and then prepared and used in the form of an oil-in-water or water-in-oil type emulsion in which they are homogeneously dispersed in a water-insoluble contrast medium (iodized oil) such as Lipiodol. Since these emulsions undergo phase separation after a period of time, they are prepared and used immediately prior to administration to a patient, and chemical embolization is performed, and gelatin sponge particles are additionally administered to promote ischemic necrosis of cancer tissue and prevent the disappearance of drugs. However, the administered emulsion has phase separation within a short time after administration, and the anticancer drug is absorbed at one time, so that the antitumor effect is not sustained and side effects due to systemic exposure are likely to occur. Further, most of the cytotoxic anticancer drugs administered in TACE are metabolized in the liver, and thus can show hepatotoxicity. For this reason, patients show a postembolization syndrome, have difficulty in daily life, and are inevitably hospitalized for 2 to 3 days, resulting in high medical costs.

Recently, selectively used chemical embolization particles (drug-eluting beads: DEBs) are a product made of non-water absorbent polyvinyl alcohol, and the like and administered by adsorbing a drug onto the embolic particles by an ion exchange method, and have a size in a range of 40 to 900 μm. The drug-eluting beads have an advantage in that compared to emulsion droplets, the particle size range is homogeneous and reproducible, and the drug is gradually released, resulting in less systemic exposure of the drug. However, the drug is not completely released after administration, less than 50% of the drug is released at 28 days after administration, and about 90% of the drug is released after 90 days, so that the drug relatively slowly accumulates at high concentration in the cancer tissue. In addition, since it takes approximately 1 to 2 hours or more to adsorb the drug, and the particles remain in the body even after the drug is completely released in a non-absorbent manner, the drug-eluting beads may induce necrosis of normal tissues, it may be difficult to perform repeated TACE procedures, and there is a risk of cancer recurrence. Furthermore, the drug cost is higher and the patient's cost burden is higher than the TACE method in the related art.

Therefore, there is a need for the development of nanoparticles that are less toxic, suitable for living organisms, and can deliver a target drug to microvessels quickly and with high efficiency.

PRIOR ART DOCUMENT

Non-Patent Document

The Korean Journal of Hepatology 2010; 16: 242-246

SUMMARY OF THE INVENTION

As a result of intensive studies to provide biocompatible nanoparticles and a preparation method thereof, which complement the problems of microbeads and inorganic nanoparticles, the present inventors have made an effort to provide a method for preparing nanoparticles by separating and purifying microparticles from the oil phase after forming a W/O emulsion using an anionic polymer, and then using a high pressure homogenizer or a mill (bead or roll) apparatus.

Therefore, an object of the present invention is to provide a composition for a vascular embolism and treating cancer, the composition including: nanoparticles including an anionic polymer and a trivalent metal compound salt; and a cationic drug; as active ingredients.

Another object of the present invention is to provide a method for preparing nanoparticles including an anionic polymer and a trivalent metal compound salt, the method including the following steps:

forming an emulsion by mixing a solution obtained by adding a water phase in which a polymer is dissolved to an oil phase with a solution in which a non-ionic surfactant is dissolved in a water phase;

forming microparticles by adding an aqueous trivalent metal compound salt solution to the emulsion; and reducing particle size of the microparticles to a nano level using one or more selected from the group consisting of a high-pressure homogenizer, a bead mill, and a roll mill.

However, a technical problem to be achieved by the present invention is not limited to the aforementioned problems, and the other problems that are not mentioned may be clearly understood by those skilled in the art from the following description.

The nanoparticles according to the present invention include carboxymethyl cellulose, which is a cellulose-based anionic polymer, and a dextran-based compound having biodegradable properties, and are less toxic and biocompatible and can deliver a drug to microvessels as being characterized by using a cross-linking agent to increase the water phase stability.

Therefore, the present invention provides a composition for a vascular embolism and treating cancer, the composition including: nanoparticles including an anionic polymer and a trivalent metal compound salt; and a cationic drug; as active ingredients.

In an exemplary embodiment of the present invention, the anionic polymer may be selected from the group consisting of carboxymethyl cellulose or a salt thereof; dextran sulfate or a salt thereof; and a mixture thereof, but is not limited thereto.

In another exemplary embodiment of the present invention, the nanoparticles may include carboxymethyl cellulose and dextran sulfate, but are not limited thereto.

In still another exemplary of the present invention, the carboxymethyl cellulose and the dextran sulfate may be included at a mass ratio of 0.5 to 20:1, but the present invention is not limited thereto.

In yet another exemplary embodiment of the present invention, the trivalent metal compound salt may be one or more selected from the group consisting of iron (III) chloride, aluminum chloride, iron nitrate $[Fe(NO_3)_3]$, aluminum nitrate $[Al(NO_3)_3]$, iron acetate $[Fe(CH_3COO)_3]$, aluminum acetate $[Al(CH_3COO)_3]$, and iron perchlorate $[Fe(ClO_4)_3]$, but is not limited thereto.

In yet another exemplary embodiment of the present invention, the cationic drug may be one or more selected from the group consisting of doxorubicin, procainamide, digoxin, quinidine, trimethoprim, cimetidine, vancomycin, irinotecan, daunorubicin, epirubicin, diphenhydramine, memantine, oxycodone, pyrilamine, and tramadol, but is not limited thereto.

In yet another exemplary embodiment of the present invention, the cationic drug may be loaded into the nanoparticles, but is not limited thereto.

In yet another exemplary embodiment of the present invention, the composition may be an emulsion formulation, but is not limited thereto.

In yet another exemplary embodiment of the present invention, the cationic drug and the nanoparticles may be included at a mass ratio of 1:1 to 10, but the present invention is not limited to thereto.

In yet another exemplary embodiment of the present invention, the composition may further include an embolic material, but is not limited thereto.

In yet another exemplary embodiment of the present invention, the embolic material may be an iodized oil, but is not limited thereto.

In yet another exemplary embodiment of the present invention, the iodized oil may be one or more selected from the group consisting of poppy fruit-derived iodized oil, soybean-derived iodized oil, and ethiodol, but is not limited thereto.

In yet another exemplary embodiment of the present invention, the nanoparticles may have a diameter of 10 to 500 nm, but the diameter is not limited thereto.

Further, the present invention provides a method for preparing nanoparticles including an anionic polymer and a trivalent metal compound salt, the method including the following steps:

forming an emulsion by mixing a solution obtained by adding an aqueous phase in which a polymer is dissolved to an oil phase with a solution in which a non-ionic surfactant is dissolved in an aqueous phase;

forming microparticles by adding an aqueous trivalent metal compound salt solution to the emulsion; and reducing particle size of the microparticles to a nano level using one or more selected from the group consisting of a high-pressure homogenizer, a bead mill, and a roll mill.

In an exemplary embodiment of the present invention, the oil may be selected from the group consisting of mineral oil, vegetable oils, heavy chain triglycerides and a mixture thereof, but is not limited thereto.

In another exemplary embodiment of the present invention, the non-ionic surfactant may be selected from the group consisting of polyvinyl alcohol, polyalkylene glycol, polyvinyl pyrrolidone, an alkyl polyglycoside, t-octylphenoxy polyethoxy ethanol, a poloxamer, polysorbate, poly(N-vinylacetamide), polyvinyl butyral, and a mixture thereof, but is not limited thereto.

In another exemplary embodiment of the present invention, the preparation method may further include: precipitating the microparticles by allowing the microparticles to stand in a separatory funnel, then separating the precipitate, and dissolving the precipitate using an organic solvent to remove impurities and oil, but is not limited thereto.

In still another exemplary embodiment of the present invention, the organic solvent may be one or more selected from the group consisting of alkyl alcohols, ketones, acetonitrile, tetrahydrofuran, and a mixture thereof, but is not limited thereto.

In yet another exemplary embodiment of the present invention, the method may further include: separating or purifying and washing the microparticles from a mixed solution including the microparticles and dissolved impurities and oils, but is not limited thereto.

In yet another exemplary embodiment of the present invention, the separation or purification of the microparticles may be performed by a centrifuge or a filter, but is not limited thereto.

In yet another exemplary embodiment of the present invention, the washing may be performed using an organic solvent selected from the group consisting of the same organic solvent or the aforementioned solvents, but is not limited thereto.

In yet another exemplary embodiment of the present invention, in the washing, it is possible to further use those selected from the group consisting of distilled water, water for injection, a water-soluble solvent in which sucrose, mannitol, sodium chloride, or the like is dissolved, and a combination thereof after the washing using the organic solvent, but the present invention is not limited thereto.

In yet another exemplary embodiment of the present invention, the method may further include: re-dispersing the purified microparticles in a water phase, and then reducing the size of the particles using a particle-size reducing apparatus, but is not limited thereto.

In yet another exemplary embodiment of the present invention, the re-dispersed water phase may be selected from the group consisting of distilled water, water for injection, a water-soluble solvent in which sucrose, mannitol, sodium chloride, or the like is dissolved, and a combination thereof, but is not limited thereto.

In yet another exemplary embodiment of the present invention, the particle-size reducing apparatus may be selected from the group consisting of a high-pressure homogenizer, a bead mill, a roll mill, and a combination thereof, but is not limited thereto.

In addition, the present invention provides a method for preparing a composition for a vascular embolism and treating cancer, the method including the following steps:

forming an emulsion by mixing a solution obtained by adding a water phase in which a polymer is dissolved to an oil phase with a solution in which a non-ionic surfactant is dissolved in a water phase;

forming microparticles by adding an aqueous trivalent metal compound salt solution to the emulsion;

reducing a particle size of the microparticles to a nano level using one or more selected from the group consisting of a high-pressure homogenizer, a bead mill, and a roll mill to prepare nanoparticles; and mixing a cationic drug with the nanoparticles.

Furthermore, the present invention provides a use of a composition including: nanoparticles including an anionic polymer and a trivalent metal compound salt; and a cationic drug; as active ingredients, for a vascular embolism and treating cancer.

Further, the present invention provides a method for performing a vascular embolization and treating cancer, the method comprising: administering, to an individual, a composition comprising: nanoparticles comprising an anionic polymer and a trivalent metal compound salt; and a cationic drug; as active ingredients.

Further, the present invention provides a use of nanoparticles including an anionic polymer and a trivalent metal compound salt; and a cationic drug; as active ingredients for preparing a drug for a vascular embolism and treating cancer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
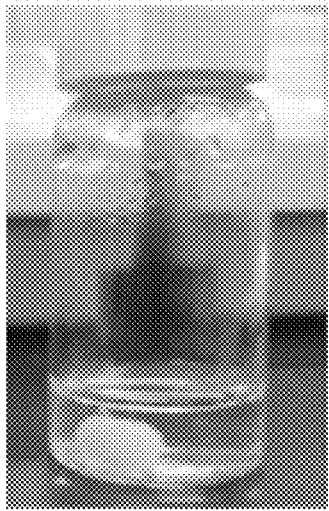
FIG. 1 illustrates a set of images of the presence or absence of changes in a reaction solution during a reaction between an anionic polymer and calcium chloride ($CaCl_2$)
Figure 1:
Figure 1:

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The nanoparticles according to the present invention include carboxymethyl cellulose, which is a cellulose-based anionic polymer, and a dextran-based compound having biodegradable properties, and are less toxic and biocompatible and can deliver a drug to microvessels as being characterized by using a cross-linking agent to increase the water phase stability.

Therefore, the present invention provides a composition for a vascular embolism and treating cancer, the composition including: nanoparticles including an anionic polymer and a trivalent metal compound salt; and a cationic drug; as active ingredients.

In an exemplary embodiment of the present invention, the anionic polymer may be selected from the group consisting of carboxymethyl cellulose or a salt thereof; dextran sulfate or a salt thereof; and a mixture thereof, but is not limited thereto.

In another exemplary embodiment of the present invention, the nanoparticles may include carboxymethyl cellulose and dextran sulfate, but are not limited thereto.

In still another exemplary embodiment of the present invention, the carboxymethyl cellulose and the dextran sulfate may be included at a mass ratio of 0.5 to 20:1, 0.5 to 15:1, 0.5 to 10:1, 0.5 to 5:1, 0.5 to 4:1, 0.5 to 2:1, 0.5 to 1:1, about 1:1, 0.5 to 3:1, 1 to 3:1, 1.5 to 2.5:1, about 2:1, 1 to 5:1, 2 to 5:1, 3 to 5:1, 3.5 to 4.5:1, 4 to 5:1, or about 4:1, 1 to 10, 1 to 9:1, 3 to 9:1, 4 to 9:1, 5 to 9:1, 6 to 9:1, 7 to 9:1, 8 to 9:1, 7.5 to 8.5:1, or about 8:1, but the mass ratio is not limited thereto.

In yet another exemplary embodiment of the present invention, the carboxymethyl cellulose and the dextran sulfate may be included at a mass ratio of preferably 8:1, 4:1, 2:1, or 1:1, but are not limited thereto.

In yet another exemplary embodiment of the present invention, the trivalent metal compound salt may be one or more selected from the group consisting of iron (III) chloride, aluminum chloride, iron nitrate [$Fe(NO_3)_3$], aluminum nitrate [$Al(NO_3)_3$], iron acetate [$Fe(CH_3COO)_3$], aluminum acetate [$Al(CH_3COO)_3$], and iron perchlorate [$Fe(ClO_4)_3$], but is not limited thereto.

In yet another exemplary embodiment of the present invention, the cationic drug may be one or more selected from the group consisting of doxorubicin, procainamide, digoxin, quinidine, trimethoprim, cimetidine, vancomycin, irinotecan, daunorubicin, epirubicin, diphenhydramine, memantine, oxycodone, pyrilamine, and tramadol, but is not limited thereto.

In yet another exemplary embodiment of the present invention, the cationic drug and the nanoparticles may be included at a mass ratio of 1:1 to 10, 1:1 to 9, 1:1 to 8, 1:1 to 7, 1:1 to 6, 1:1 to 5, 1:1 to 4, 1:1 to 3, 1:1 to 2.5, 1:2 to 2.5, or 1:1 to 1.5, but are not limited thereto.

In yet another exemplary embodiment of the present invention, the cationic drug and the nanoparticles may be included at a dry weight ratio of 1:1 to 10, 1:1 to 9, 1:1 to 8, 1:1 to 7, 1:1 to 6, 1:1 to 5, 1:1 to 4, 1:1 to 3, 1:1 to 2.5, or 1:2 to 2.5, or 1:1 to 1.5.

In yet another exemplary embodiment of the present invention, the composition may further include an embolic material, but is not limited thereto.

In yet another exemplary embodiment of the present invention, the embolic material may be an iodized oil, but is not limited thereto.

In yet another exemplary embodiment of the present invention, the iodized oil may be one or more selected from the group consisting of poppy fruit-derived iodized oil, soybean-derived iodized oil, and ethiodol, but is not limited thereto. Lipiodol may be used as a product name of the poppy fruit-derived iodized oil, but the product name is not limited thereto.

In yet another exemplary embodiment of the present invention, the nanoparticles may have a diameter of 10 to 500 nm, 10 to 400 nm, 10 to 300 nm, 10 to 250 nm, 10 to 200 nm, 10 to 180 nm, 10 to 160 nm, 10 to 150 nm, 10 to 140 nm, 30 to 500 nm, 30 to 400 nm, 30 to 300 nm, 30 to 250 nm, 30 to 200 nm, 30 to 180 nm, 30 to 160 nm, 30 to 150 nm, 30 to 140 nm, 50 to 500 nm, 50 to 400 nm, 50 to 300 nm, 50 to 250 nm, 50 to 200 nm, 50 to 180 nm, 50 to 160 nm, 50 to 150 nm, 50 to 140 nm, 70 to 500 nm, 70 to 400 nm, 70 to 300 nm, 70 to 250 nm, 70 to 200 nm, 70 to 180 nm, 70 to 160 nm, 70 to 150 nm, 70 to 140 nm, but are not limited thereto.

In yet another exemplary embodiment of the present invention, the cationic drug may be loaded in a form bound to anions present inside and on the surface of the nanoparticles.

In yet another embodiment of the present invention, the vascular embolization may be, as transarterial chemoembolization (TACE), a method for treating cancer by injecting an anticancer drug into an artery going into a cancer tissue and using an embolic material to block the supply of nutrients.

In yet another exemplary embodiment of the present invention, the cancer includes an angiogenesis-dependent cancer, and is preferably one or more selected from the group consisting of liver cancer, ovarian cancer, breast cancer and non-small cell lung cancer, and more preferably liver cancer. A stable emulsion may be formed by binding a cationic drug to the nanoparticles according to an exemplary embodiment of the present invention, and then mixing the cationic drug with iodized oil, and an embolic effect may be enhanced by injecting the emulsion into the hepatic artery.

The composition of the present invention may be provided in the form of an emulsion, but is not limited thereto.

The composition of the present invention is characterized by being administered within 0 to 2 hours, preferably 0 to 1 hour after preparation, and as the transfer of the drug in the nanoparticles is kept lower for a long period of time than the composition used for chemical embolization in the related art, stability is excellent.

In the present invention, the composition including the nanoparticles and the cationic drug and the embolic material may be mixed using a mixing method using a 3-way cock, a method using ultrasonic waves, or the like, but is not limited thereto.

Furthermore, the present invention provides a method for forming a vascular embolism and preventing or treating cancer, the method including: administering the composition to an individual.

The content of the nanoparticles and the cationic anticancer agent in the composition of the present invention can be appropriately adjusted according to the symptoms of the disease, the degree of progression of the symptoms, the condition of the patient, and the like, and may be, for example, 0.0001 to 99.9 wt %, or 0.001 to 50 wt %, but is not limited thereto. The content ratio is a value based on a dry amount from which the solvent is removed.

The pharmaceutical composition of the present invention may further include an appropriate carrier, an appropriate excipient, and an appropriate diluent, which are typically used to prepare a pharmaceutical composition. The excipient may be, for example, one or more selected from the group consisting of a diluent, a binder, a disintegrant, a lubricant, an adsorbent, a moisturizer, a film-coating material, and a controlled release additive.

Examples of a carrier, an excipient or a diluent which may be included in the composition according to the present invention include lactose, dextrose, sucrose, an oligosaccharide, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

When the composition is prepared, the composition is prepared using a diluent or excipient, such as a filler, an extender, a binder, a wetting agent, a disintegrant, and a surfactant, which are commonly used.

As an additive for liquid formulation according to the present invention, it is possible to use water, diluted hydrochloric acid, diluted sulfuric acid, sodium citrate, sucrose monostearates, polyoxyethylene sorbitol fatty acid esters (twin esters), polyoxyethylene monoalkyl ethers, lanolin ethers, lanolin esters, acetic acid, hydrochloric acid, aqueous ammonia, ammonium carbonate, potassium hydroxide, sodium hydroxide, prolamin, polyvinyl pyrrolidone, ethyl cellulose, carboxymethyl cellulose sodium, and the like.

As a syrup according to the present invention, a solution of sucrose, other sugars or sweeteners, and the like may be used, and a fragrance, a colorant, a preservative, a stabilizer, a suspending agent, an emulsifier, a thickener, and the like may be used, if necessary.

Purified water may be used for the emulsion according to the present invention, and an emulsifier, a preservative, a stabilizer, a fragrance, and the like may be used, if necessary.

As the suspending agent according to the present invention, a suspending agent such as acacia, tragacanth, methyl cellulose, carboxymethyl cellulose, carboxymethyl cellulose sodium, microcrystalline cellulose, sodium alginate, hydroxypropyl methyl cellulose, HPMC 1828, HPMC 2906, and HPMC 2910 may be used, and a surfactant, a preservative, a colorant, and a fragrance may be used, if necessary.

The injection according to the present invention may include: a solvent such as distilled water for injection, 0.9% sodium chloride injection, Ringer's injection, dextrose injection, dextrose+sodium chloride injection, PEG, lactated Ringer's injection, ethanol, propylene glycol, non-volatile oil-sesame oil, cottonseed oil, peanut oil, corn oil, ethyl oleate, isopropyl myristate, and benzoic acid benzene; a solubilizing agent such as sodium benzoate, sodium salicylate, sodium acetate, urea, urethane, monoethyl acetamide, butazolidin, propylene glycol, Tweens, nijungtinateamide, hexamine, and dimethylacetamide; a buffer such as a weak acid or a salt thereof (acetic acid and sodium acetate), a weak base and a salt thereof (ammonia and ammonium acetate), an organic compound, a protein, albumin, peptone, and gums; an isotonic agent such as sodium chloride; a stabilizer such as sodium bisulfite ($NaHSO_3$), carbon dioxide gas, sodium metabisulfite ($Na_2S_2O_5$), sodium sulfite ($Na_2SO_3$), nitrogen gas ($N_2$), and ethylenediaminetetraacetic acid; a sulfating agent such as 0.1% sodium bisulfide, sodium formaldehydesulfoxylate, thiourea, disodium ethylenediaminetetraacetate, and acetone sodium bisulfite; an analgesic such as benzyl alcohol, chlorobutanol, procaine hydrochloride, glucose, and calcium gluconate; and a suspending agent such as carboxymethyl cellulose sodium, sodium alginate, Tween 80, and aluminum monostearate.

The pharmaceutical composition according to the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including type of disease of patients, the severity of disease, the activity of drugs, sensitivity to drugs, administration time, administration route, excretion rate, treatment period, and simultaneously used drugs, and other factors well known in the medical field.

The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by a person with ordinary skill in the art to which the present invention pertains.

The pharmaceutical composition of the present invention is determined by the type of drug that is an active ingredient, as well as various related factors such as the disease to be treated, the route of administration, the age, sex, and body weight of a patient, and the severity of the disease.

As used herein, the individual refers to a subject in need of treatment of a disease, and more specifically, may be a mammal such as a human or a non-human primate, a mouse, a rat, a dog, a cat, a horse, and a cow, but is not limited thereto.

The administration as used herein refers to the provision of a predetermined composition of the present invention to an individual by any suitable method.

As used herein, the prevention refers to all actions that suppress or delay the onset of a target disease, and the treatment refers to all actions that ameliorate or beneficially change a target disease and the resulting metabolic abnormalities by administration of the pharmaceutical composition according to the present invention, and the amelioration refers to all actions that reduce a target disease and associated parameters, for example, the degree of symptoms, by administration of the composition according to the present invention.

Further, the present invention provides a method for preparing nanoparticles including an anionic polymer and a trivalent metal compound salt, the method including the following steps:

☐) forming an emulsion by mixing a solution obtained by adding a water phase in which a polymer is dissolved to an oil phase with a solution in which a non-ionic surfactant is dissolved in a water phase;

☐) forming microparticles by adding an aqueous trivalent metal compound salt solution to the emulsion; and iii) reducing particle size of the microparticles to a nano level using one or more selected from the group consisting of a high-pressure homogenizer, a bead mill, and a roll mill.

The above items relating to the composition may be applied to the present preparation method.

Step i) may include one or more selected from the group consisting of the following Steps a) to d), but is not limited thereto.

Step ii) may include the following Step(s) e) and/or f), but is not limited thereto.

Step iii) may include the following Step 1), but is not limited thereto.

The method for preparing nanoparticles may include a step of stirring each component so as to be uniformly mixed between each step, but is not limited thereto.

The method may include h) separating microparticles from the oil phase between Steps ii) and iii), but is not limited thereto.

The method may include i) removing residual oils and side-reaction products by adding an organic solvent to a solution including microparticles between Steps ii) and iii).

In the present invention, the emulsion may be in the form of W/O, but is not limited thereto.

For the W/O emulsion, the ratio of the water phase and the oil phase may be 1:1 to 50, 1:1 to 40, 1:1 to 30, 1:1 to 20, 1:1 to 15, 1:1 to 10, 1:1 to 9, 1:1 to 8, 1:1 to 7, 1:1 to 6, 1:2 to 6, 1:3 to 6, 1:2 to 5, 1:3 to 5, 1:50, 1:40, 1:30, 1:20, 1:10, 1:9, 1:8, 1:7, 1:6, 1:5, 1:4, 1:3, or 1:2, but is not limited thereto. In the present invention, the higher the proportion of oil, the better the emulsion formation, but the optimum ratio for minimally using oil may be preferably about 1:4.

In the present invention, the method may further include: separating or purifying and washing the microparticles from a mixed solution including the microparticles and dissolved impurities and oils, but is not limited thereto.

In the present invention, the preparation method may further include: precipitating the microparticles by allowing the microparticles to stand in a separatory funnel, then separating the precipitate, and dissolving the precipitate using an organic solvent to remove impurities and oil, but is not limited thereto.

In the present invention, the separation or purification of the microparticles may be performed by a centrifuge or a filter, but is not limited thereto.

In the present invention, the washing may be performed using an organic solvent selected from the group consisting of the same organic solvent or the aforementioned solvents, but is not limited thereto.

In the present invention, in the washing, it is possible to further use those selected from the group consisting of distilled water, water for injection, a water-soluble solvent in which sucrose, mannitol, sodium chloride, or the like is dissolved, and a combination thereof after the washing using the organic solvent, but the present invention is not limited thereto.

In the present invention, the method may further include: re-dispersing the purified microparticles in a water phase, and then reducing the size of the particles using a particle-size reducing apparatus, but is not limited thereto.

In the present invention, the re-dispersed water phase may be a water-soluble solvent in which one or more selected from the group consisting of distilled water, water for injection, sucrose, mannitol, and sodium chloride are dissolved, but is not limited thereto.

In the present invention, the particle-size reducing apparatus may be selected from the group consisting of a high-pressure homogenizer, a bead mill, a roll mill, and a combination thereof, but is not limited thereto.

In the present invention, the time for performing the reducing of the particle size of the microparticles to a nano level may be flexibly adjusted according to the amount of nanoparticles, and generally, the crushing time is extended as the amount of nanoparticles is increased.

The method for preparing nanoparticles of the present invention may include one or more of the following steps or consist of the following steps, but is not limited thereto:

a) dissolving an anionic polymer in a water phase,
b) preparing a first solution to which the water phase in step a) is added while stirring the oil phase using a homogenizer,
c) adding a second solution of a non-ionic surfactant dissolved in a water phase to the solution in step b),
d) forming an emulsion while stirring the solution in step c) using a homogenizer,
e) forming microparticles by adding a cross-linking agent separately dissolved in a water phase to the emulsion in step d),
f) further performing stirring in step e),
g) separating layers by allowing the solution in step f) to stand,
h) separating the microparticles from the oil phase,
i) extracting and/or removing residual oils and side-reaction products by adding an organic solvent to a solution including the microparticles,
j) separating and/or removing the residual organic solvent from the microparticles using an aqueous solution,
k) diluting the microparticles in the water phase,
l) preparing nanoparticles by reducing the particle size of the microparticles diluted in the aqueous solution using a high-pressure homogenizer, a bead mill, or a roll mill, and
m) concentrating the nanoparticles dispersed in the aqueous solution using centrifugation or ultrafiltration.

Steps a) to c) may be performed in a suitable order.

Furthermore, the steps are not necessarily limited to the order described above.

In the present invention, the oil phase may be selected from the group consisting of mineral oil, vegetable oils, heavy chain triglycerides and a mixture thereof, but is not limited thereto.

In the present invention, the mineral oil is also called mineral oil, is a by-product produced in the process of refining crude oil, and is an oil including alkanes and paraffin as main components.

In the present invention, the vegetable oil may be an oil derived from nuts, seeds, grains, or the like, and may include, for example, peanut oil, soybean oil, coconut oil, olive oil, or the like.

In the present invention, the heavy chain triglyceride is a representative alternative fat prepared by hydrolyzing coconut oil and palm oil, and then fractionating caprylic acid and capric acid, and again esterifying (or bonding) the same with glycerol. The heavy chain triglyceride is a heavy chain fatty acid usually having 8 to 10 carbon atoms, and has a small molecular structure.

In the present invention, the non-ionic surfactant may be selected from the group consisting of polyvinyl alcohol, polyalkylene glycol, polyvinyl pyrrolidone, an alkyl polyglycoside, t-octylphenoxy polyethoxy ethanol, a poloxamer, polysorbate, poly(N-vinylacetamide), polyvinyl butyral, and a mixture thereof, but is not limited thereto.

In the present invention, as the polyalkylene glycol, typical polyalkylene glycols known in the art can be used without limitation, but it is preferred to use polyethylene glycol.

In the present invention, the poloxamer is a non-ionic triblock copolymer in which hydrophilic ethylene oxide is bonded to both ends with hydrophobic propylene oxide as the center, and has a characteristic of temperature sensitivity, and thus, can convert sol and gel depending on the concentration and temperature, and the properties of the poloxamer differ depending on the ratio of polyoxypropylene and polyoxyethylene. The poloxamer may be selected from the group consisting of Poloxamer 101, Poloxamer 105, Poloxamer 105 benzoate, Poloxamer 108, Poloxamer 122, Poloxamer 123, Poloxamer 124, Poloxamer 181, Poloxamer 182, Poloxamer 182 dibenzoate, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, and Poloxamer 407, but is not limited thereto.

In the present invention, the alkyl polyglycoside may be selected from the group consisting of, for example, a $C_{8-22}$ alkyl glycoside, more specifically, caprylyl glucoside, coco-glucoside, decyl glucoside, lauryl glucoside, methyl coco glucoside and myristyl glucoside, but is not limited thereto.

In the present invention, the organic solvent may be one or more selected from the group consisting of alkyl alcohols, ketones, acetonitrile, tetrahydrofuran, and a mixture thereof, but is not limited thereto.

The alkyl alcohols may be alcohols having 1 to 6 carbon atoms, and may be, for example, methanol, ethanol, industrial alcohol, propanol, butanol, pentanol, and hexanol, but are not limited thereto.

The ketones may be organic solvents having a chemical formula of RCOR, and may be acetone, methyl ethyl ketone, methyl butyl ketone, cyclohexanone, methyl isobutyl ketone, diisobutyl ketone and the like, but are not limited thereto.

In addition, the present invention provides a method for preparing a composition for a vascular embolism and treating cancer, the method including the following steps:

forming an emulsion by mixing a solution obtained by adding a water phase in which a polymer is dissolved to an oil phase with a solution in which a non-ionic surfactant is dissolved in a water phase;

forming microparticles by adding an aqueous trivalent metal compound salt solution to the emulsion;

reducing a particle size of the microparticles to a nano level using one or more selected from the group consisting of a high-pressure homogenizer, a bead mill, and a roll mill to prepare nanoparticles; and mixing a cationic drug with the nanoparticles.

The mixing of the cationic drug with the nanoparticles may be performed by treating ultrasonic waves, but is not limited thereto.

The method for preparing a composition for a vascular embolism and treating cancer may further include mixing a mixed composition of the nanoparticles and the cationic drug with an embolic material, but is not limited thereto.

The mixing of the mixed composition with the embolic material may be performed using a mixing method using a 3-way cock, a method using ultrasonic waves, or the like, but is not limited thereto.

As used herein, the term ultrasonic waves (ultrasound) refers to a sound wave exceeding the frequency of 16 Hz to 20 kHz, which is the frequency of a sound wave generally audible to the human ear, and high-intensity concentrated ultrasonic waves may exhibit an instantaneous thermal effect (65 to 100° C.), a cavitation effect, a mechanical effect, and a sonochemical effect depending on the energy and frequency by introducing focused ultrasonic waves that provide continuous and high-intensity ultrasonic energy to the focal point. Ultrasonic waves do no harm as they pass through human tissues, but the high-intensity ultrasonic waves that form the focal point generates energy enough to cause coagulative necrosis and heat ablation effects, regardless of tissue type. In the present invention, the ultrasonic wave refers to a sound wave having a frequency higher than an audible frequency range of 16 Hz to 20 kHz.

Throughout the specification of the present invention, when one part "includes" one constituent element, unless otherwise specifically described, this does not mean that another constituent element is excluded, but means that another constituent element may be further included. Throughout the specification of the present invention, a term of a degree, such as "about" or "substantially", is used as meaning a corresponding numerical value or used as a meaning close to the numerical value when a natural manufacturing and a material tolerance error are presented in a described meaning, and is used to prevent an unconscientious infringer from illegally using disclosed contents including a numerical value illustrated as being accurate or absolute in order to help understanding of the present invention.

Throughout the specification of the present invention, the term "combination thereof" included in the Markush type expression means a mixture or combination of one or more selected from the group consisting of constituent elements described in the Markush type expression, and means including one or more selected from the group consisting of the above-described constituent elements.

In the present specification (especially in the claims), the use of the aforementioned terms and similar indicating terms may correspond to singular and plural forms. In addition, the case where a range is described includes individual values belonging to the above range are included (unless there is a description contrary to this), and is the same as the description of individual values constituting the above range in the Detailed Description. Finally, the above steps may be performed in a suitable order, unless the steps constituting the method are clearly ordered or described contrary to this. The steps are not necessarily limited to the order described above. The use of all examples or exemplary terms (for example, and the like) is merely to illustrate the technical idea in detail and, unless limited by the claims, the range is not limited by the above examples or exemplary terms. Furthermore, those skilled in the art can also know that the steps may be constituted by design conditions or factors within the scope of the claims or their equivalents to which various modifications, combinations and alterations are added.

Terms such as first and second may be used to explain various constituent elements, but the constituent elements are not limited by the terms. The terms are used only to distinguish one constituent element from another constituent element. For example, without departing from the scope of the invention, a first constituent element may be called a second constituent element, and similarly, the second constituent element may be called the first constituent element. The term and/or includes a combination of a plurality of related described items, or any item among the plurality of related described items.

Since the present invention may be modified into various forms and include various exemplary embodiments, specific exemplary embodiments will be illustrated in the drawings and described in detail in the Detailed Description. However, the description is not intended to limit the present invention to the specific exemplary embodiments, and it is to be understood that all the changes, equivalents, and substitutions belonging to the spirit and technical scope of the present invention are included in the present invention. When it is determined that the detailed description of the related publicly known art in describing the present invention may obscure the gist of the present invention, the detailed description thereof will be omitted.

Hereinafter, preferred Examples for helping the understanding of the present invention will be suggested. However, the following examples are provided only to more easily understand the present invention, and the contents of the present invention are not limited by the following examples.

EXAMPLES

Example 1. Reactivity Confirmation Test of Polymer and Cross-Linking Agent

In order to compare the reactivity of an anionic polymer with calcium chloride, reactivity was tested by adding calcium chloride in the presence of carboxymethyl cellulose.

Example 1-1. Reactivity Test 1

2 mL of 0.2% CMC and 2 mL of 0.2% carboxymethyl dextran sodium (hereinafter, referred to as CMD) were put into a 20 mL vessel, and 0.5 mL of 10% calcium chloride was added thereto with stirring. No solid was formed when checked for 1 hour.

Example 1-2. Reactivity Test 2

Reactivity was confirmed by increasing the concentration to perform a test on each composition of the following Table 1 in the same manner as in <Reactivity Test 1>.

As illustrated in FIG. 1, in the case of Composition 1, there was no change, and in the case of Compositions 2 and 3, the compositions were changed to suspensions.

Figure 2:
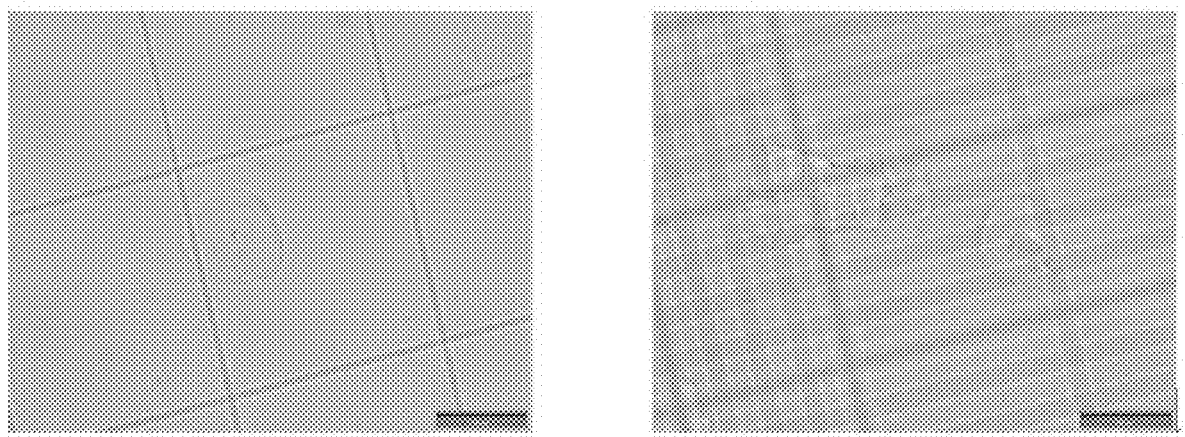
FIG. 2 illustrates optical microscope measurement images of the solid produced through Composition 2 of Example 1-2, "Reactivity Test 2"

Further, as illustrated in FIG. 2, as a result of confirming optical microscope analysis images for the reaction solid of Composition 2 in Table 1, it could be confirmed that the reaction solid was gelled without being granulated.

According to the results, it was confirmed that calcium chloride was not suitable as a cross-linking agent for preparing nanoparticles.

TABLE 1

Composition of Reactivity Test 2

| No. | CMC | CMD | $CaCl_2$ | Whether microparticles are formed |
|---|---|---|---|---|
| Composition 1 | — | 20% | 5% | Not formed as clear solution |
| Composition 2 | 7% | — | 5% | As a result of confirming suspension under microscope, reaction solid was gelled without forming particles |
| Composition 3 | 7% | 20% | 5% | As a result of confirming suspension under microscope, reaction solid was gelled without forming particles |

Example 2. Preparation of Microparticles Using W/O Emulsion

A CMC solution, an iron chloride (FeCl$_3$) solution, and a dextran sulfate (DS) powder were each prepared according to the composition ratios in the following Table 2.

First, the DS powder was dissolved in the CMC solution, mixed with a 1% polyvinyl alcohol (hereinafter, referred to as PVA) solution at room temperature, and then the resulting mixture was added dropwise to a medium chain triglyceride (hereinafter, referred to as MCT) oil used as an oil phase, and an emulsion was prepared using an ultrasonic disperser (sonicator). After FeCl$_3$ was added dropwise to the emulsion, particles were prepared by further stirring the resulting mixture. Centrifugation was performed at 4° C. and 15,000 rpm for 10 minutes to obtain the formed particles, and insoluble materials and the MCT oil were removed using ethanol. Ethanol and purified water were used to sequentially perform separation using a centrifuge under the same conditions, and finally, the resulting product was re-dispersed in 2 mL of purified water.

TABLE 2

Test compositions and conditions

| No. | CMC | DS | PVA | Sonication time | W/O Ratio | FeCl$_3$ | Cross-linking time |
|---|---|---|---|---|---|---|---|
| Compositon 1 | 0.50%, 0.5 mL | 10 mg | 1%, 0.5 mL | 90 s | 1:20 | 0.50% | 2 hr |
| Composition 2 | 0.50%, 0.5 mL | 10 mg | 1%, 0.5 mL | 90 s | 1:5 | 0.40% | 2 hr |
| Composition 3 | 0.50%, 0.5 mL | 10 mg | 1%, 0.5 mL | 180 s | 1:20 | 0.40% | 2 hr |
| Composition 4 | 0.10%, 0.5 mL | 10 mg | 1%, 0.5 mL | 90 s | 1:40 | 0.40% | 2 hr |
| Composition 5 | 0.10%, 0.5 mL | 10 mg | 1%, 0.5 mL | 90 s | 1:20 | 0.40% | 2 hr |
| Composition 6 | 0.50%, 0.5 mL | 10 mg | 1%, 0.5 mL | 90 s | 1:40 | 0.40% | 2 hr |

As a result, particles were successfully formed with an increasing sonication time as the CMC concentration was increased.

Example 3. Confirmation of Yield According to Preparation of Microparticles Using W/O Emulsion A homogenizer was used instead of the ultrasonic disperser for scale-up. The homogenizer (rpm: 17,000) was used to prepare particles according to the composition ratios shown in the following Table 3 by the same preparation method at room temperature, and the yields according to respective composition ratios were compared. The mass after drying was measured by lyophilizing each of the finally re-dispersed suspensions.

Figure 3:
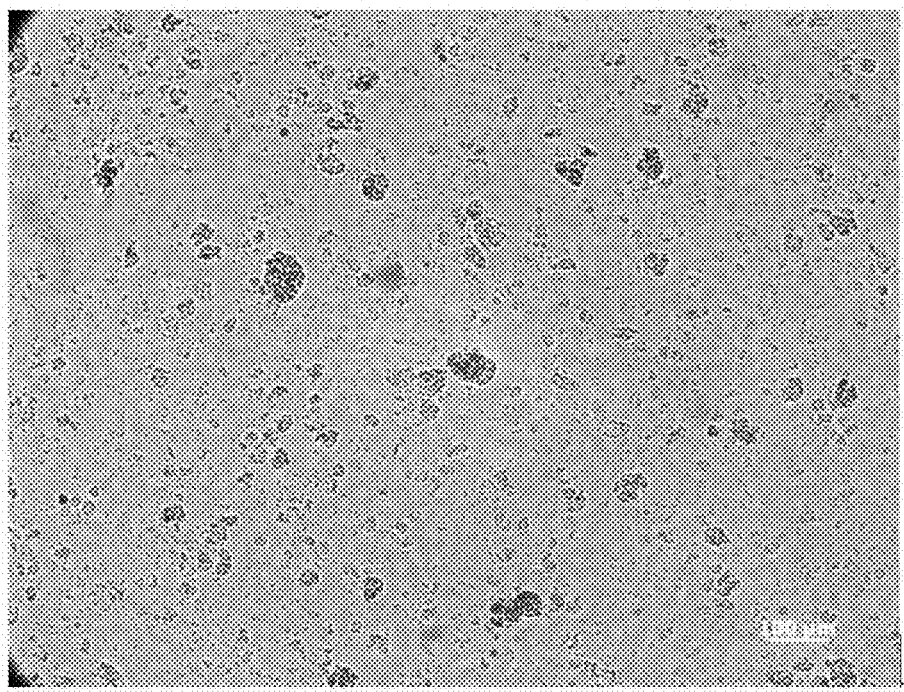
FIG. 3 illustrates an image of microparticles prepared by the reaction of an anionic polymer with iron chloride according to Composition 2 of Example 3 and Table 3.

As illustrated in FIG. 3, from the image of the solid produced by Composition 2 in Table 3, it could be seen that particles were formed when iron chloride was used rather than when calcium chloride was used.

As shown in Table 3, it was confirmed that the highest yield was obtained when CMC and DS were mixed at a mass ratio of 2:1.

TABLE 3

Test composition, conditions, obtained amount, and yield

| No. | CMC | DS | PVA (mass %) | Homogenization Time | W/O Ratio | Crosslinking agent (mass %) | Cross-linkage Time | Obtained amount | Yield |
|---|---|---|---|---|---|---|---|---|---|
| Composition 1 | 1%, 100 mL, (1 g) | 2 g | 2%, 100 mL | 10 min | 1:4 | 2.5% FeCl$_3$, 100 mL | 30 min | 1.08 g | 36.0% |
| Composition 2 | 1%, 100 mL, (1 g) | 0.5 g | 2%, 100 mL | 10 min | 1:4 | 2.5% FeCl$_3$, 100 mL | 30 min | 0.83 g | 79.0% |

TABLE 3-continued

Test composition, conditions, obtained amount, and yield

| No. | CMC | DS | PVA (mass %) | Homogenization Time | W/O Ratio | Crosslinking agent (mass %) | Cross-linkage Time | Obtained amount | Yield |
|---|---|---|---|---|---|---|---|---|---|
| Composition 3 | 1%, 100 mL, (2 g) | 1 g | 2%, 100 mL | 10 min | 1:4 | 2.5% $FeCl_3$, 100 mL | 30 min | 1.01 g | 50.5% |
| Composition 4 | 2%, 100 mL, (2 g) | 0.5 g | 2%, 100 mL | 10 min | 1:4 | 2% $AlCl_3$, 100 mL | 30 min | 1.23 g | 49% |

(however, the yield excludes the cross-linking agent content)

Example 4. Preparation of Nanoparticles Through Additional Nanoprocessing after Preparation of Microparticles Using W/O Emulsion The preparation of microparticles was implemented by the following method. To prepare a water phase solution, 2 g of PVA and 1 g of CMC were each dissolved in 100 mL of distilled water. Then, 0.5 g of DS was measured, added to the CMC solution, and then dissolved. To prepare a cross-linking agent solution, 0.5 g of iron (III) chloride ($FeCl_3$) was dissolved in 100 mL of distilled water.

To prepare a W/O emulsion, a 2 L beaker was filled with 800 mL of the MCT oil, and all of the water phase solutions were added while being stirred at room temperature at 17,000 rpm using a homogenizer. After the mixture was stirred under the same conditions for 10 minutes, the cross-linking agent solution was added dropwise thereto, and the resulting mixture was further stirred for about 30 minutes.

Microparticles were separated using the following experimental method: The reaction solution was transferred to a separatory funnel and allowed to stand for about 2 hours. The lower layer liquid (water phase) in which the yellow solid was present in the separatory funnel was collected and yellow particle pellets were produced using a centrifuge. The supernatant was discarded, and a white material was dissolved and removed using ethanol. In this case, care was taken not to affect the pellets in the lower layer. 15 mL of ethanol was added thereto, the pellet was re-dispersed using a vortex and ultrasonic disperser, and the re-dispersion was repeated until no aggregates were visible. And then, microparticles were obtained by repeating the washing process sequentially with distilled water and a sucrose (5%) solution in addition to ethanol. Finally, the microparticles were re-dispersed in the 5%-sucrose solution.

To prepare nanoparticles, a bead mill (Minicer, Netzsch) was used. Nanoparticles were prepared in an amount of about 500 mL by diluting the above washed particles in the 5%-sucrose solution. Small particles were prepared by performing milling at a pump speed of 20 rpm, a flow rate of 5 m/s, and about 10° C. using 0.2-mm beads. After the beads were replaced with 0.1-mm beads, particles having an average size of 146.6 nm (PDI: 0.145) were obtained by further performing milling at a pump speed of 10 rpm, a flow rate of 4 m/s, and the same temperature.

Figure 4:
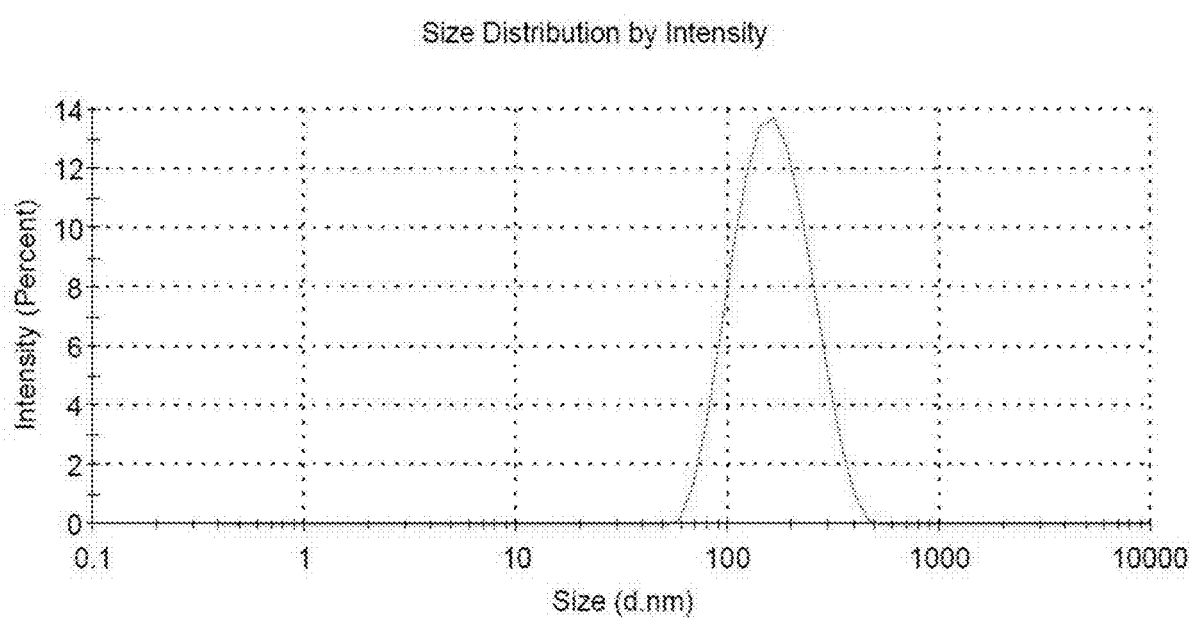
FIG. 4 illustrates the results of measuring a particle distribution graph of nanoparticles prepared using a bead mill, using dynamic light scattering (DLS)

As illustrated in FIG. 4, as a result of a dynamic light scattering (DLS) measurement, the particle distribution was found to be 50 nm to 460 nm.

Figure 5:
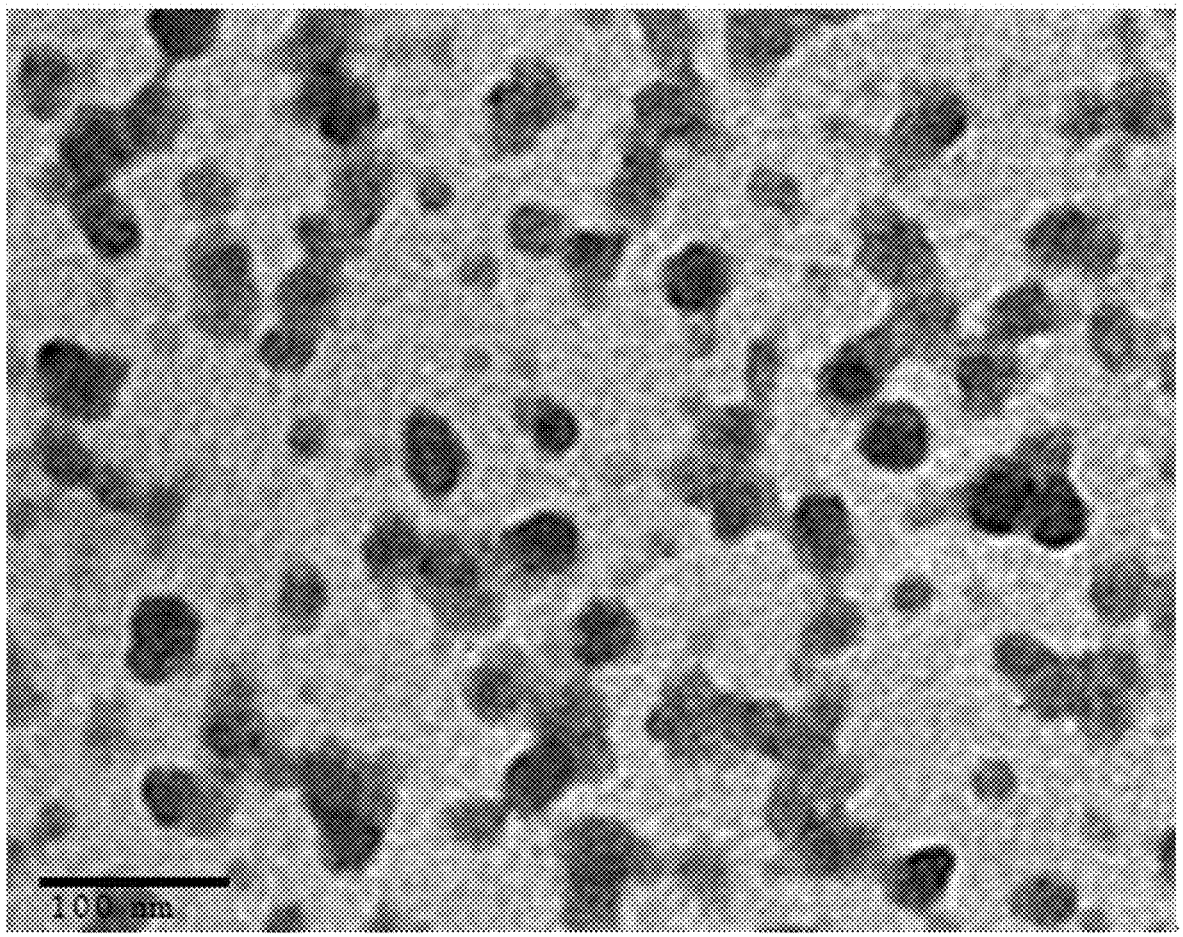
FIG. 5 illustrates an image of TEM measurement of nanoparticles prepared using a bead mill.

Further, as illustrated in FIG. 5, it was confirmed that nano-sized particles were successfully produced by the nanoprocessing.

Example 5. Preparation and Elution Test of Nanoparticles Loaded with Doxorubicin Hydrochloride Doxorubicin hydrochloride was completely dissolved at a concentration of 25 mg/mL in a 5%-sucrose solution. A ratio of doxorubicin hydrochloride: particles=25 mg: 6 mg was adjusted by putting a completely dissolved doxorubicin hydrochloride sucrose solution into a 1.25-mL 5%-sucrose solution in which 60 mg of nanoparticles were dispersed, and the resulting mixture was additionally mixed for about 30 minutes after an initial bath type sonication treatment for 1 minute.

500 µL of the nanoparticle suspension loaded with the doxorubicin hydrochloride was put into a CelluSep membrane (MW: 15,000, Width: 32 mm, Wall thickness: 24 µm), and both sides were blocked with clips. 50 mL of a buffer (PVA 0.4%, Tween 0.1% in lactic acid pH=2.7, and 37° C.) was put into a vial and stirred at 200 rpm, and the temperature was increased to 37° C. The membrane sample was put thereinto and an elution test was performed. The amount of doxorubicin eluted was confirmed by measuring the absorbance of the sample taken for each point with a UV spectrophotometer (wavelength: 475 nm).

Figure 6:
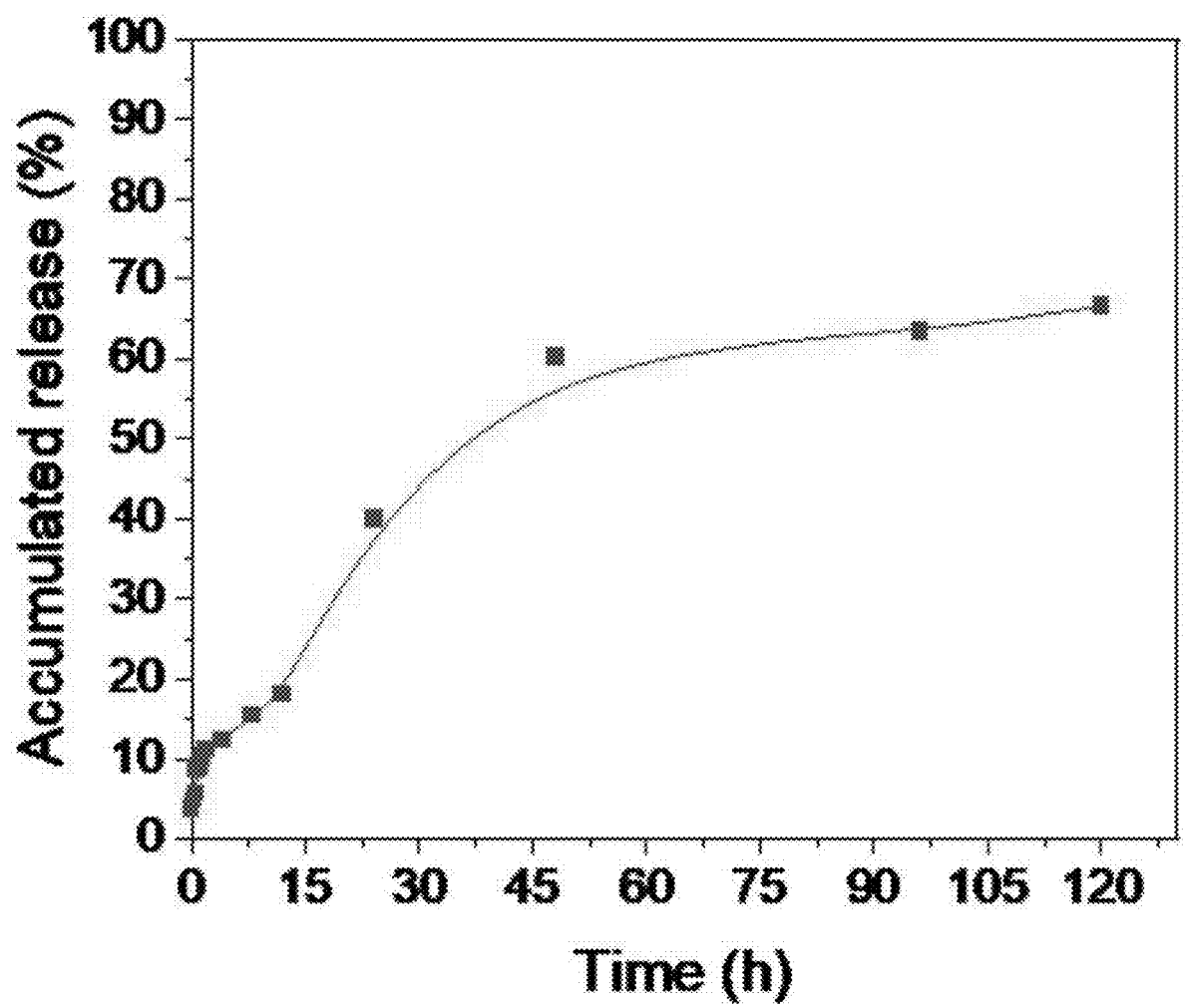
FIG. 6 illustrates a graph of drug elution after loading a cationic drug (doxorubicin hydrochloride)

As a result, as illustrated in FIG. 6, it was found that the amount of doxorubicin eluted was about 70%, which is excellent.

Example 6. In Vitro Cytotoxicity Evaluation

Viability analysis was performed on Huh7 liver cancer cells to evaluate the toxicity of the prepared nanoparticles. Three groups were evaluated: doxorubicin hydrochloride (dox), particles loaded with doxorubicin (032d), and particles not loaded with doxorubicin (032).

Figure 7:
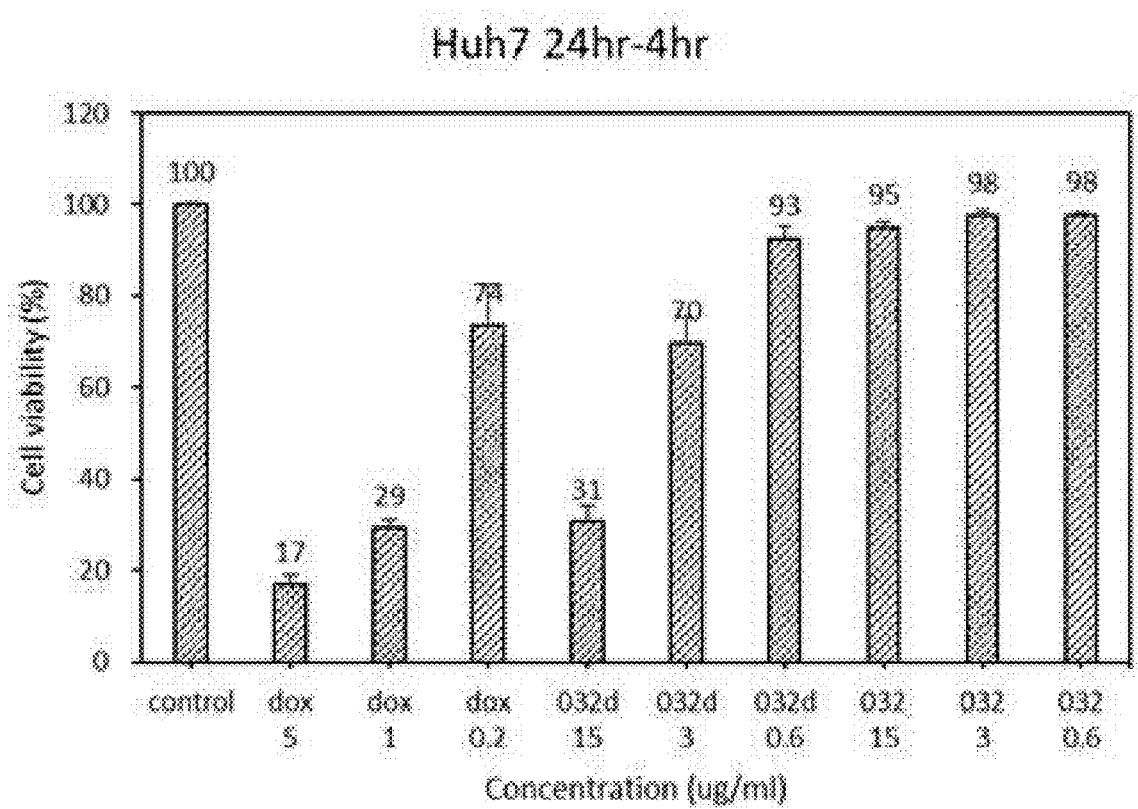
FIG. 7 illustrates the results of measuring cell viability in Huh7 cells.

As illustrated in FIG. 7, it was confirmed that the particles loaded with the same drug as the doxorubicin hydrochloride itself showed a cancer cell killing effect in a concentration-dependent manner, whereas the particles not loaded with the drug had no killing effect regardless of the concentration, and thus did not show toxicity.

Figure 8:
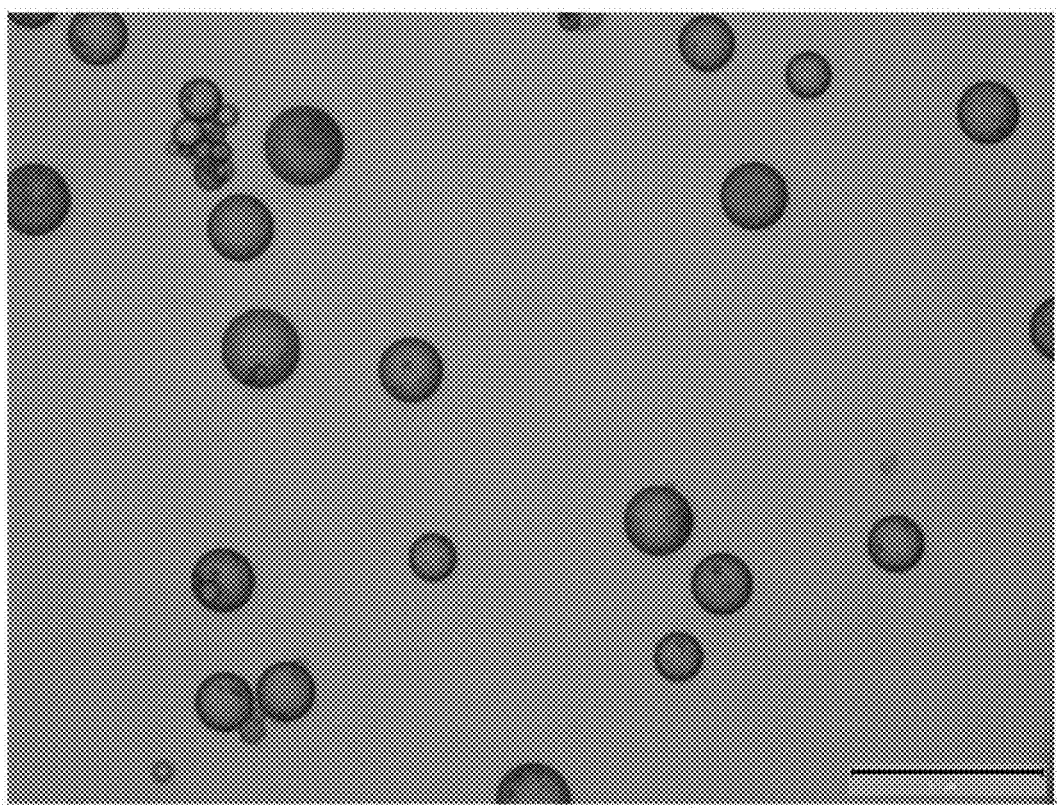
FIG. 8 illustrates an optical microscopy image of an emulsion of a nanoparticle suspension aqueous solution loaded with a cationic drug and a Lipiodol ultra solution.

Example 7. Preparation of Mixed Emulsion with Lipiodol and Confirmation of Passage Through Microcatheter After the drug was dissolved by putting 1.25 mL of Omnipaque 300 injection (GE Healthcare) into a vial containing 50 mg of doxorubicin hydrochloride (Ildong Adriamycin-RDF), the whole amount was taken using a syringe, a suspension of naoparticles loaded with the drug was prepared by putting the drug-dissolved solution into a solution of 60 mg of the nanoparticles dissolved in 2 mL of the 5%-sucrose solution. Then, 10 mL of a Lipiodol ultra solution (Guerbet Korea) was prepared in a separate syringe. An emulsion was prepared by placing the two solutions in a 3-way cock and alternately pressing the syringes. An image of the formed emulsion is illustrated in FIG. 8.

A microcatheter was connected to the last side of the 3-way cock containing the prepared emulsion, and the prepared emulsion was allowed to pass by pressing the syringe. In the same manner, a microcatheter passage test was compared with an emulsion prepared by replacing the 5%-sucrose solution with a 15%-mannitol solution.

Figure 9:
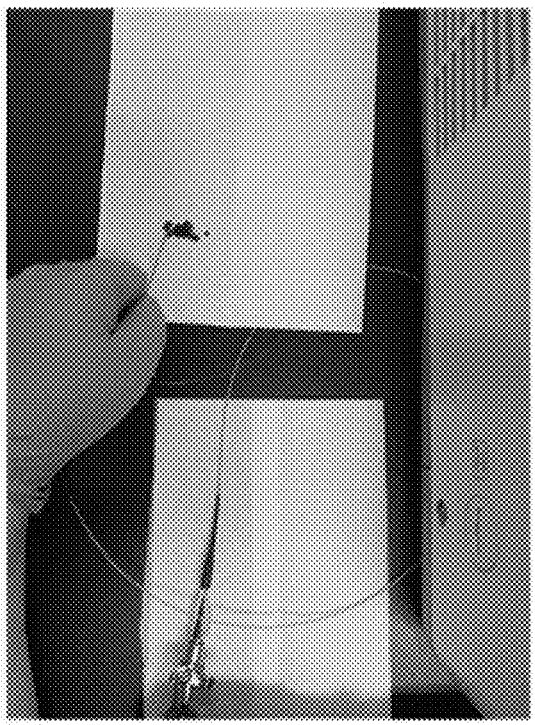
FIG. 9 illustrates microcatheter passage images of a mixed emulsion of each suspension using 5%-sucrose and 15%-mannitol as a drug-loaded aqueous suspension and a Lipiodol ultra solution.
Figure 9:
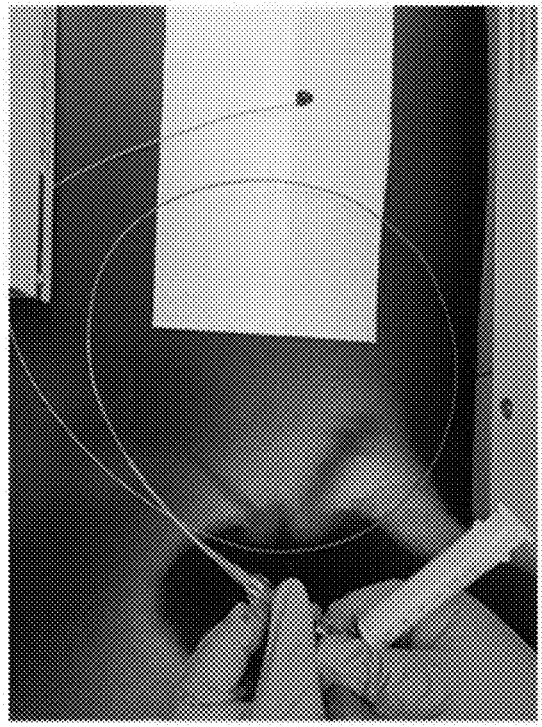

As a result, as illustrated in FIG. 9, both cases passed through the microcatheter.

Therefore, it was confirmed that the emulsion prepared by the method of the present invention could be used for embolization by passing through a microcatheter.

The present invention provides a novel method for preparing nanoparticles which are useful for the delivery of a cationic drug, are less toxic and biocompatible, and can deliver the drug to microvessels, and the novel preparation method according to the present invention exhibits the effect of enabling mass production at an industrial level.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described examples are illustrative only in all aspects and are not restrictive.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for performing a vascular embolization and treating cancer, the method comprising: administering, to an individual, a composition comprising: nanoparticles comprising an anionic polymer and a trivalent metal compound salt; and
a cationic drug; as active ingredients.

2. The method of claim 1, wherein the anionic polymer is selected from the group consisting of carboxymethyl cellulose or a salt thereof dextran sulfate or a salt thereof and a mixture thereof.

3. The method of claim 1, wherein the nanoparticles comprise carboxymethyl cellulose and dextran sulfate.

4. The method of claim 3, wherein the carboxymethyl cellulose and the dextran sulfate are comprised at a mass ratio of 0.5 to 20:1.

5. The method of claim 1, wherein the trivalent metal compound salt is one or more selected from the group consisting of iron (III) chloride, aluminum chloride, iron nitrate [Fe(NO3)3], aluminum nitrate [Al(NO3)3], iron acetate [Fe(CH3COO)3], aluminum acetate [Al(CH3COO)3], and iron perchlorate [Fe(ClO4)3].

6. The method of claim 1, wherein the cationic drug is one or more selected from the group consisting of doxorubicin, procainamide, digoxin, quinidine, trimethoprim, cimetidine, vancomycin, irinotecan, daunorubicin, epirubicin, diphenhydramine, memantine, oxycodone, pyrilamine, and tramadol.

7. The method of claim 1, wherein the cationic drug is loaded into the nanoparticles.

8. The method of claim 1, wherein the composition is an emulsion formulation.

9. The method of claim 1, wherein the cationic drug and the nanoparticles are comprised at a mass ratio of 1:1 to 10.

10. The method of claim 1, further comprising an embolic material.

11. The method of claim 10, wherein the embolic material is an iodized oil.

12. The method of claim 11, wherein the iodized oil is one or more selected from the group consisting of poppy fruit-derived iodized oil, soybean-derived iodized oil, and ethiodol.

13. The method of claim 1, wherein the nanoparticles have a diameter of 10 to 500 nm.

14. The method of claim 1, wherein the nanoparticles are prepared by the method comprising the following steps:
forming an emulsion by mixing a solution obtained by adding a water phase in which a polymer is dissolved to an oil phase with a solution in which a non-ionic surfactant is dissolved in a water phase;
forming microparticles by adding an aqueous trivalent metal compound salt solution to the emulsion; and
reducing particle size of the microparticles to a nano level using one or more selected from the group consisting of a high-pressure homogenizer, a bead mill, and a roll mill.

15. The method of claim 1, wherein the composition is prepared by the method comprising the following steps:
forming an emulsion by mixing a solution obtained by adding a water phase in which a polymer is dissolved to an oil phase with a solution in which a non-ionic surfactant is dissolved in a water phase;
forming microparticles by adding an aqueous trivalent metal compound salt solution to the emulsion;
reducing a particle size of the microparticles to a nano level using one or more selected from the group consisting of a high-pressure homogenizer, a bead mill, and a roll mill to prepare nanoparticles; and
mixing a cationic drug with the nanoparticles.

* * * * *